United States Patent [19]

Brookhart et al.

[11] Patent Number: 5,892,101
[45] Date of Patent: Apr. 6, 1999

[54] CROSS-DIMERIZATION OF OLEFINS

[75] Inventors: Maurice S. Brookhart, Chapel Hill, N.C.; Elisabeth Muriel Hauptman, Wilmington, Del.

[73] Assignee: E. I. du Pont de Nemours and Company, Wilmington, Del.

[21] Appl. No.: 899,857

[22] Filed: Jul. 24, 1997

Related U.S. Application Data

[60] Provisional application No. 60/031,070, Nov. 18, 1996.

[51] Int. Cl.[6] .................................................... C07C 69/52
[52] U.S. Cl. ........................ 560/205; 502/152; 556/138; 526/126
[58] Field of Search .............................................. 560/205

[56] References Cited

U.S. PATENT DOCUMENTS

| | | | |
|---|---|---|---|
| 4,692,548 | 9/1987 | Drent | 560/202 |
| 5,175,326 | 12/1992 | Klabunde | 526/126 |
| 5,324,847 | 6/1994 | Laufenberg | 554/162 |

FOREIGN PATENT DOCUMENTS

| | | |
|---|---|---|
| 2243064 | 3/1973 | Germany . |
| 122720 | 5/1994 | Japan . |
| 9623010 | 8/1996 | WIPO . |

OTHER PUBLICATIONS

Wolfgang Beck et al., "Metal Complexes of Weakly Coordinating Anions. Precursors of Strong Cationic Organometallic Lew Acids", Chem. Rev., 88, 1405–1421, 1988.
Steven H. Strauss, "The Search for Larger and More Weakly Coordinating Anions", Chem. Rev., 93, 927–942.
G. Wilke et al., Angew. Chem. Int. Ed. Engl., 27, 185, 1988.
G. Wilke et al., Angew. Chem. Int. Ed. Engl., 5, 151 & 897, 1966.
G. Wilke et al., Angew. Chem. Int. Ed. Engl., 5, 582, 1966.
Hoberg, H. et al J. Organomet. Chem (1986) 307 (2) C41–C43.

Primary Examiner—Paul J. Killos

[57] ABSTRACT

Disclosed is a process for the production of chemical intermediates by the cross dimerization of two compounds containing carbon-carbon double bonds, wherein said process is catalyzed by a nickel II catalyst which is a complex with $\eta^3$ carbon-based allyl or substituted allyl, trisubstituted phosphine, and a weakly coordinating ligand. This catalyst may be used to selectively cross-dimerizes ethylene and methyl acrylate to give methyl 4-pentenoate, a nylon 6,6 intermediate.

14 Claims, No Drawings

CROSS-DIMERIZATION OF OLEFINS

This application claims the priority benefit of U.S. Provisional Application 60/031,070, filed Nov. 18, 1996.

FIELD OF INVENTION

This invention concerns a process for the production of chemical intermediates by the cross dimerization of two compounds containing carbon-carbon double bonds. Specifically provided is a process for the production of methyl 4-pentenoate (M4P) by selectively cross-dimerizing ethylene and methyl acrylate. Methyl 4-pentenoate is a nylon 6,6 intermediate.

TECHNICAL BACKGROUND

This invention concerns a process for the production of valuable chemical intermediates by the cross dimerization of two compounds containing carbon-carbon double bonds. Specifically provided is a process for the production of methyl 4-pentenoate (M4P).

It is generally known to use nickel catalysts in the dimerization, oligomerization, and polymerization of olefins.

The present invention, however, provides a novel process which is a highly selective route to methyl 4-pentenoate, an intermediate in the manufacture of adipic acid, via cross-dimerization. Adipic acid is one of the starting materials in the manufacture of nylon 6,6.

G. Wilke et al., *Angew. Chem.* Int. Ed. Engl. (1988), 27, 185, report the polymerization of ethylene to linear polyethylene by a nickel catalyst.

G. Wilke et al., *Angew. Chem.* Int. Ed. Engl. (1988), 27, 185, present a general review on Ni-catalyzed dimerization, oligomerization and polymerization of olefins.

G. Wilke et al., *Angew. Chem.* Int Ed. Engl. (1966), 5, 151, and 897, and *Angew. Chem.,* Int. Ed. Engl. (1966), 5, 582, disclose general procedures for preparing allyl-nickel-halide and allyl-nickel-methyl complexes. No detailed experimental procedures were reported.

Laufenberg (U.S. Pat. No. 5,324,847) discloses methods of preparing ethylene adducts of polyunsaturated 18–22 carbon fatty acids or alkyl esters in the presence of Ru, Rh, Pd, Ir, and Pt-containing catalysts.

Drent (U.S. Pat. No. 4,692,548) discloses methods of reacting acrylate esters and ethene using Ru or Pd compounds along with Ag or Cu salts.

SUMMARY OF THE INVENTION

Disclosed is a process for the preparation of methyl 4-pentenoate, which comprises contacting ethylene with methyl acrylate in the presence of a nickel II catalyst complex of the structure $[QNiL_1L_2]^+X^-$, wherein $Q=\eta^3$ carbon-based allyl or substituted allyl $L_1$=a monodentate trisubstituted phosphine ligand $L_2$=a weakly coordinating ligand $X$=a non-coordinating or weakly coordinating nonreactive anion;

any liquid medium that may be present as solvent or diluent being non-reactive under the conditions of the process and non-coordinating; and recovering the crude reaction product.

Optionally, methyl 4-pentenoate can be separated from the crude reaction product by conventional methods, although the crude reaction product often can be used in further reactions without separating methyl 4-pentenoate.

DETAILED DESCRIPTION OF THE INVENTION $L_1$, a monodentate trisubstituted phosphine, is defined as $PR_1R_2R_3$, where each of $R_1$, $R_2$, and $R_3$ is independently a linear, branched, or cyclic hydrocarbon up to 20 carbon atoms; two of $R_1$, $R_2$, and $R_3$ can form a ring. Preferably, $R_1$, $R_2$, and $R_3$ are identical and are hexyl, methyl, or phenyl. The most preferred $R_1$, $R_2$, or $R_3$ is cyclohexyl.

Weakly-coordinating ligands are defined as ligands that are easily displaced from a metal. Examples of such weakly-coordinating ligands are dialkyl ethers or nitriles of aliphatic acids. Preferably $L_2$ is derived from the solvent used in the reaction; more preferably, $L_2$ is acetonitrile, diethyl ether, or tetrahydrofuran.

Weakly coordinating anions are known to those skilled in the art. Such anions are often bulky anions, particularly those that may delocalize their negative charge. The coordinating capability of such anions has been discussed in the literature; see, for instance, W. Beck, et al., *Chem. Rev.,* vol.88, p.1405–1421 (1988), and S. H. Strauss, *Chem. Rev.,* Vol.93, p.927–942 (1993). The preferred weakly coordinating anions of the present are $[B(3,5—(CF_3)_2C_6H_3)_4]^-$ and $[B(C_6F_5)_4]^-$.

The preferred catalyst is selected from the group consisting of:

$(\eta^3—C_3H_5)Ni(PCy_3)(OEt_2)^+BAr'_4^-$;

$(\eta^3—C_3H_5)Ni(PCy_3)(NCCH_3)^+BAr'_4^-$;

$(\eta^3—C_3H_5)Ni(P(2—CH_3OC_6H_4)_3)(NCCH_3)^+BAr'_4^-$; and $(\eta^3—C_3H_5)Ni(P(CH_3)_3)(OEt_2)^+BAr'_4^-$;

and the in situ formed catalyst systems:

$(\eta^3—C_3H_5)Ni(PCy_3)(CH_3)+H(OEt_2)_2^+BAr'_4^-$;

$(\eta^3—C_3H_5)Ni(COD)^+BAr'_4^-+PCy_3$; and $(\eta^3—C_3H_5)Ni(COD)^+BAr'_4^-+P(2—CH_3OC_6H_4)_3$;

where Cy=cyclohexyl; Ar'=3,5—(CF$_3$)$_2$C$_6$H$_3$—, and COD=1,5-cyclooctadiene.

The general procedures used to prepare the catalysts are illustrated in Equations 1–8. Allyl chloride is reacted with nickel(O) dicyclooctadiene to form diallyl-dichloro-dinickel (II) complex (Equation 1).

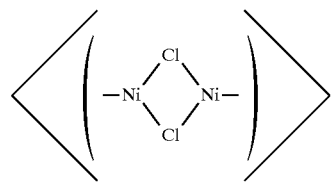

Equation 1

The notation used at both ends of the formula on the right hand side of the equation represents a delocalized allyl complex with Ni.

This complex is reacted with the phosphine ligand $L_1$ to form an allyl-chloro-phosphine-nickel complex (Equation 2).

Equation 2

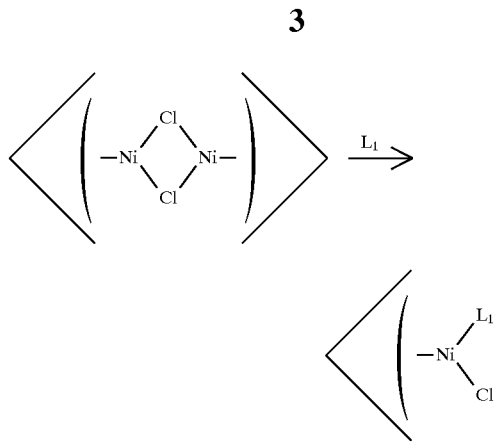

The chlorine atom is replaced with an R group by reacting the complex with an RMgBr Grignard reagent (Equation 3).

Equation 3

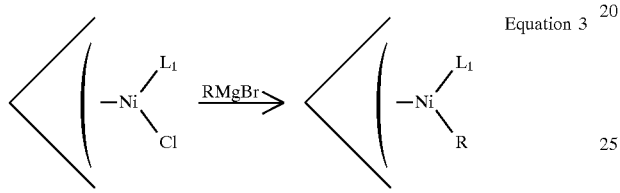

The resulting complex is reacted with $L_2$ and with the boron compound $HBAr'_4$ to form the desired catalyst (Equation 4).

Equation 4

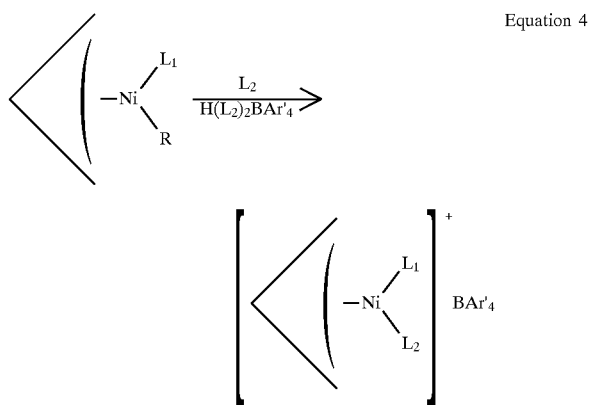

An alternate synthesis route involves reacting the allyl-chloro-phosphine-nickel complex with $L_2$ and the Na form of the boron salt (Equation 5).

Equation 5

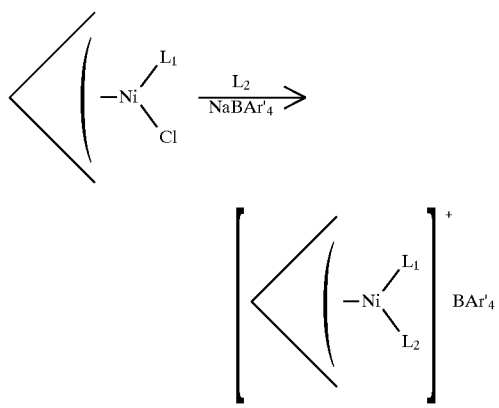

The compound $(\eta^3-C_3H_5)Ni(COD)^+BAr'_4{}^-$ is prepared by reacting the diallyl-dichloro-dinickel complex from Equation 1 directly with COD and $NaBAr'_4$ (Equation 6).

Equation 6

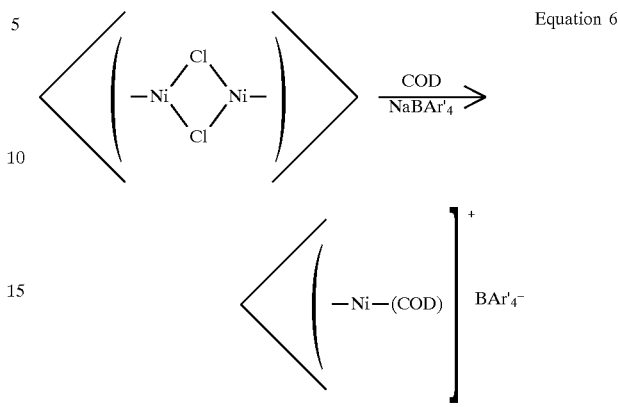

The cross-dimerization process is preferably carried out in a non-reacting, weakly coordinating solvent. Non-reacting, weakly-coordinating solvents are defined as solvents that are not coordinated to the metal or, if they are, they can be easily displaced from the metal. Non-reactive is defined as not reacting in the present invention. Aprotic organic solvents such as halogenated aromatic solvents, e.g., monochlorobenzene and o-dichlorobenzene are typically employed. Most preferred are methylene chloride, and excess of neat methyl acrylate.

The process can be carried out at any convenient pressure. Normally, the pressure can vary from about 14 to about 120 psia (96 to 827 kPa). The preferred pressure range is from about 28 to about 69 psia (69 to about 476 kPa).

A temperature range typically employed is from about 0 to about 100° C. Preferred temperature range is from about 15 to about 60° C.

The process is sensitive to oxygen and moisture and is preferably carried out in an atmosphere of an inert gas, ethylene (which is a reactant) or in a mixture of inert gas and ethylene, in the absence of oxygen and moisture. Typical inert gases are nitrogen and argon. The reacting mixture is preferably agitated.

The dimerization reactions are shown in Equations 7 and 8, below.

Equation 7

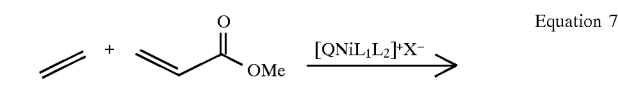

Equation 8

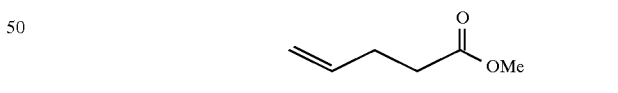

In the Experiments and Examples the following abbreviations are used:
Cy=cyclohexyl
Ar'=3,5—$(CF_3)_2C_6H_3$—
COD is 1,5-cyclooctadiene
M4P=methyl 4-pentenoate
M3P=methyl 3-pentenoate M2P is methyl 2-pentenoate Me=methyl Et=ethyl TO is turnover; number of moles of cross-dimer formed per mole of catalyst.

EXAMPLES

General Information

All complexes were manipulated in an atmosphere of dry, oxygen-free nitrogen within a dry box or on a standard Schlenk line. Methylene chloride was distilled in a nitrogen atmosphere from phosphorus pentoxide prior to use. Toluene, hexane, and diethyl ether were distilled in a nitrogen atmosphere from sodium and benzophenone prior to use. $^1$H and $^{13}$C NMR spectra were recorded on either a Varian XL-400, Bruker WM-200, a Bruker WM-250, or GE-300 spectrometer. Chemical shifts were reported by reference to protonated residues of solvents. Elemental analyses were performed by Oneida Research Services, Inc., Whitesboro, N.Y. Gas chromatography (GC) analyses were conducted on a 30-meter DB-210 column from J&W Scientific, Folsom, Calif., using flame ionization detection. $Ni(COD)_2$ was purchased from Strem Chemicals, Inc., Newbury, Mass. Some of the following preparations have been reported in the literature but have limited detailed experimental sections. Most of the compounds have not been previously fully characterized.

"Experiments" reported herein describe the preparation of the catalysts used. "Examples" describe the cross-dimerization of ethylene with methyl acrylate.

Experiment 1

Preparation of $[Ni(C_3H_5)Cl]_2$

The synthesis of this complex was described by G. Wilke et al., *Angew. Chem., Int. Ed. Engl.* 1966, 5, 151. A 500 ml round-bottomed flask was charged with 5.033 g (18.3 mmol) of $Ni(COD)_2$ suspended in 250 ml of diethyl ether. The solution was cooled to −78° C. and 1.5 ml (18.4 mmol) of allyl chloride was added dropwise. The mixture was allowed to warm to ambient temperature and was stirred for 2 hours, during which time the yellowish suspension turned into a deep red solution. The solvent was removed in vacuum and the product was extracted with about 110 ml of hexane. These extracts were filtered and the filtrates placed at −30° C. to cause crystallization. Red crystals (2.07 g, 84% yield) were recovered. $^1$H NMR (300 MHz, 23° C., $C_6D_6$); δ4.81 (m, 1H, $CH_2$—CH—$CH_2$), 2.64 (d, 2H, $J_{cis}$=6.9 Hz, $H_{cis}$), 1.63 (d, 2H, $J_{trans}$=13.1 Hz, $H_{trans}$)

EXPERIMENT 2

Preparation of $(C_3H_5)NiClPCy_3$

A Schlenk flask was charged with $[Ni(C_3H_5)Cl]_2$ (204.1 mg, 0.75 mmol) and tricyclohexylphosphine (429 mg, 1.53 mmol). The flask was cooled to −78° C., and $Et_2O$ (60 ml) was added with stirring. The reaction mixture was warmed to 23° C. and stirred for 30 min. The solvent was removed at a reduced pressure. The solid residue was extracted with 4×10 ml of diethyl ether; the extracts were filtered and placed at −25 to −30° C., at which temperature crystallization occurred. The yield was 455 mg (73%). $^1$H NMR (400 MHz, 23° C., $C_6D_6$); δ4.92 (m, central allylic H); 4.17 (m, 1H, $H_{cis}$), 3.12 (dd, J=14 and 5 Hz, 1H, $H_{trans}$), 2.30 (br, 1H, $H_{cis}$), 1–2.2 (m, $PCy_3$). The missing $H_{trans}$ was probably obscured by the tricyclohexylphosphine resonances. $^{13}$C NMR (100 MHz, 23° C., $C_6D_6$); δ108.7 (d, $J_{C-H}$=159 Hz, central allylic C), 74.8 (dt, $J_{C-P}$=20 Hz, $J_{C-H}$=161 Hz, allylic C trans to P), 43.8 (dt, $J_{P-C}$=7 Hz, $J_{C-H}$=153 Hz, allylic C cis to P), 34.0 (dd, $J_{P-C}$=18 Hz, $J_{C-H}$=121 Hz, cyclohexyl C α to P), 30.3 (t, $J_{C-H}$=126 Hz, cyclohexyl C γ to P), 27.9 (dt, $J_{C-H}$=117 Hz, $J_{P-C}$=10 Hz, cyclohexyl C β to P), 26.8 (t, $J_{C-H}$=123 Hz, cyclohexyl C para). Analysis: Found (Calcd.): C, 60.95 (60.68); H. 9.47 (9.21).

Experiment 3

Preparation of $(C_3H_5)NiClPMe_3$

A Schlenk flask was charged with $[Ni(C_3H_5)Cl]_2$ (426 mg, 1.58 mmol) dissolved in 50 ml of diethyl ether. The solution was cooled to −78° C. and 3.15 ml of a 1M solution of $PMe_3$ in toluene (3.15 mmol) was added dropwise. At −78° C., a solid immediately formed but upon warming to 23° C. redissolved. The red-orange mixture was stirred at 23° C. for 1 hour, and the solvent was removed at a reduced pressure. The product was extracted with 20 ml of diethyl ether; the extracts were filtered and the filtrates placed at −30° C. to cause crystallization. The yield was 504 mg (76%). $^1$H NMR (300 MHz, 23° C., $CD_2Cl_2$); δ5.32 (m, central allylic H); 3.92 (m, 1H, $H_{cis}$), 2.99 (dd, J=14 and 6 Hz, 1H, $H_{trans}$), 2.66 (brdd, 1H, $H_{Cis}$), 1.82 (brd, J=13 Hz, 1H, $H_{trans}$), 1.32 (d, $J_{P-H}$=9 Hz, 9H, $P(CH_3)_3$). $^{13}$C NMR (75 MHz, 23° C., $CD_2Cl_2$); δ110.9 (d, $J_{C-H}$=160 Hz, central allylic C), 73.1 (dt, $J_{C-P}$=22 Hz, $J_{C-H}$=156 Hz, allylic C trans to P), 46.5 (dt, JP–C=6 Hz, $J_{C-H}$=152 Hz, allylic C cis to P), 14.6 (dq, JP–C=27 Hz, $J_{C-H}$=130 Hz, $P(CH_3)_3$). Analysis: Found (Calcd.): C, 34.14 (34.11); H. 6.47 (6.68).

Experiment 4

Preparation of $(C_3H_5)(PCy_3)Ni(CH_3)$

A Schlenk flask was charged with 191 mg (0.46 mmol) of $(C_3H_5)(PCy_3)NiCl$, prepared as above, dissolved in 15 ml of $Et_2O$ (red-orange solution). The flask was cooled to −78° C., at which temperature 165 ml of a 3M solution of MeMgBr in $Et_2O$ (0.5 mmol) was added dropwise. The solution, which immediately lightened in color, with MgBrCl precipitating, was stirred at −78° C. for 90 min. The solution was filtered to a flask kept at −78° C. The cold bath was removed and as the reaction mixture was warming the solvent was removed under vacuum. The orange-yellow solid residue was extracted with hexane and recrystallized at −78° C. (139 mg, 77% yield). $^1$H NMR (300 MHz, 23° C., $C_6D_6$); δ4.91 (dddd, $2J_{trans}$=14 Hz, $2J_{cis}$=7 Hz, central allylic H), 3.49 (ddd, $J_{cis}$=7 Hz, J=5 Hz, J=3 Hz, 1H, $H_{cis}$), 2.92 (ddd, $J_{cis}$=7 Hz, 2J=3 Hz, 1H $H_{cis}$), 2.63 (dd, $J_{trans}$=14 Hz, J=5 Hz, 1H, $H_{trans}$), the missing $H_{trans}$ was probably obscured by the cyclohexyl signals, 1–2.2 (m, cyclohexyl), 0.15 (d, 3H, $J_{P-H}$=7 Hz, Ni—$CH_3$). $^{13}$C NMR (75 MHz, 23° C., C6D6); δ109.3 (d, $J_{C-H}$=154 Hz, central allylic C), 60.8 (dt, $J_{C-P}$=22 Hz, $J_{C-H}$=158 Hz, allylic C trans to P), 53.5 (dt, $J_{P-C}$=5 Hz, $J_{C-H}$=152 Hz, allylic C cis to P), 35.2 (dd, $J_{P-C}$=18 Hz, $J_H$=123 Hz, cyclohexyl C α to P), 30.5 (t, $J_{C-H}$=126 Hz, cyclohexyl C γ to P), 30.4 (t, $J_{C-H}$=126 Hz, cyclohexyl C γ to P), 28.1 (t, $J_{C-H}$=118 Hz, cyclohexyl C β to P), 28.0 (t, $J_{C-H}$=118 Hz, cyclohexyl C β to P), 26.9 (t, $J_{C-H}$=122 Hz, cyclohexyl C para), −16.1 (dq, $J_{P-C}$=16 Hz, $J_{C-H}$=122 Hz, Ni—$CH_3$).

Experiment 5

Preparation of $[(C_3H_5)(PCy_3)Ni(Et_2O)]^+[BAr'_4]^−$

A Schlenk flask was charged with 53.4 mg (0.13 mmol) of $(C_3H_5)(PCy_3)Ni(CH_3)$ and 143 mg (0.14 mmol) of H(Et$_2$O)$_2$BAr'$_4$. The flask was cooled to −78° C., and 3.5 ml of Et$_2$O was added. The solution was slightly warmed to allow for the complete dissolution and reaction of the reactants. Once complete dissolution had occurred, the flask was kept at −78° C. for 15 min. At that time, 2×10 ml of hexane was added, causing the precipitation of the yellow product. After stirring at −78° C. for an additional hour, the surnatant was discarded, the remaining solid was washed with hexane and dried under vacuum. Recrystallization from Et$_2$O/hexane at −30° C. yielded 99.5 mg (ca 58%) of a mixture of diethyl ether (30%) and water (70%) complexes. A $^1$H NMR spectrum at −80° C. was recorded before recrystallization: $^1$H NMR (300 MHz, −80° C., CD$_2$Cl$_2$); δ7.72 (s, 8H, Ar'), 7.54 (s, 4H, Ar'), 5.62 (m, central allylic H), 4.36 (d, J$_{cis}$=7 Hz, 1H, H$_{cis}$) 3.83 (brq, J=7 Hz, 2H, (CH$_3$CHHO)$_2$), 3.78 (brq, J=7 Hz, 2H, (CH$_3$CHHO)$_2$), 3.64 (brm, 1H), 3.52 (brm, 1H), 3.19 (dd, J=4 and 14 Hz, 1H, H$_{trans}$), 1–2.6 (m, cyclohexyl and (CH$_3$CH$_2$O)$_2$). The $^{13}$C NMR spectrum was recorded after recrystallization, confirming the presence of a mixture of H$_2$O (1) and Et$_2$O (2) complexes: $^{13}$C{H} NMR (100 MHz, −60° C., CD$_2$Cl$_2$); δ counterion signals, 115.1 (s, central allylic (1)), 75.1 (d, J$_{C-P}$=15 Hz, allylic C trans to P (2)), 74.3 (d, J$_{C-P}$=15 Hz, allylic C trans to P (1)), 71.0 (s, (CH$_3$CH$_2$O)$_2$), 42.6 (s, allylic C cis to P (1)), 40.3 (s, allylic C cis to P (2)), 24–36 (cyclohexyl carbons), 14.3 (s, (CH$_3$CH$_2$O)$_2$). Analysis: (mixture of complexes) Found (Calcd.): C, 50.54 (50.92); H. 4.68 (4.29).

Experiment 6

Preparation of [(C$_3$H$_5$)(PCy$_3$)Ni(CH$_3$CN)]$^+$[BAr'$_4$]$^−$

A Schlenk flask was charged with 40.3 mg (0.097 mmol) of (C$_3$H$_5$)Ni(PCy$_3$)Cl and 88 mg (0.099 mmol) of NaBAr'$_4$. The flask was cooled to −78° C., at which temperature 50 μl (0.96 mmol) of CH$_3$CN was added (it froze along the side). Ten ml of Et$_2$O was added with a syringe, rinsing the acetonitrile into the flask to the reactants. The flask was warmed up to 23° C. and stirred for ca 45 min. The clear yellow solution became cloudy as NaCl formed. The solution was filtered, and the solvent was removed from the filtrate under vacuum, yielding a glassy yellow solid (116 mg, 93% yield). $^1$H NMR (300 MHz, 23° C., CD$_2$Cl$_2$); δ7.72 (s, 8H, Ar'), 7.57 (s, 4H, Ar'), 5.46 (m, central allylic H), 4.45 (brd, J$_{cis}$=7 Hz, $^1$H, H$_{cis}$), 3.25 (brd, J$_{trans}$=13 Hz, 1H, H$_{trans}$), 3.10 (br, 1H, H$_{cis}$) 2.37 (s, 3H, CH$_3$CN), 2.10 (brd, J=13 Hz, 1H, H$_{trans}$), 1.0–2.0 (m, cyclohexyl). $^{13}$C NMR (100 MHz, 23° C., CD$_2$Cl$_2$); δ162.2 (q, J$_{C-B}$=50 Hz, C$_1$'), 135.2 (d, J$_{C-H}$=159 Hz, C$_2$'), 130.9 (s, CH$_3$CN), 129.3 (q, J$_{C-F}$=35 Hz, C$_3$'), 125.0 (q, J$_{C-F}$=272 Hz, CF$_3$), 117.9 (dd, $^4$J$_{C-F}$=4 Hz, J$_{C-H}$=164 Hz, C$_4$'), 116.1 (d, J$_{C-H}$=162 Hz, central allylic carbon), 78.2 (brt, J$_{C-H}$=162 Hz, allylic C), 51.3 (brt, J$_{C-H}$170 Hz, allylic C), 34.8 (dd, J$_{C-P}$=20 Hz, J$_{C-H}$=125 Hz, cyclohexyl C to P), 30.5 (t, J$_{C-H}$=128 Hz, cyclohexyl C γ to P), 28.0 (dt, J$_{P-C}$=11 Hz, J$_{C-H}$=128 Hz, cyclohexyl C β to P), 26.5 (t, J$_{C-H}$=135 Hz, cyclohexyl C para), 4.2 (q, J$_{C-H}$=140 Hz, CH$_3$CN). Analysis: Found (Calcd.): C, 51.69 (51.43); H. 3.88 (4.16); N. 1.00 (1.09).

Experiment 7

Preparation of (C$_3$H$_5$)(PMe$_3$)Ni(CH$_2$SiMe$_3$)

A Schlenk flask was charged with 205 mg (0.97 mmol) of (C$_3$H$_5$)(PMe$_3$)NiCl prepared as above dissolved in 40 ml of Et$_2$O (orange solution). The flask was cooled to −78° C., at which temperature 1.05 ml of a 1M solution of Me$_3$Si—CH$_2$MgBr in Et$_2$O (1.05 mmol) was slowly added with a syringe into the solution. The solution, which turned immediately from orange to yellow, was stirred at −78° C. for 2 hours. The cold bath was removed, and, as the mixture was warmed, the solvent was removed under vacuum. The yellow-brown solid was extracted with 3×5 ml of hexane (a brownish color resulted from some decomposition). Hexane was removed from the filtrate, yielding an orange oil (179 mg, 66% yield). The product was pure by $^1$H NMR spectroscopy. $^1$H NMR (300 MHz, 23° C., C$_6$D$_6$); δ4.72 (m, central allylic H), 3.55 (dt, J=7.3 Hz, 2J=2.3 Hz, 1H, H$_{cis}$), 2.56 (d, J=6.6 Hz, 1H, H$_{cis}$) 2.40 (d, J=13.8 Hz, 1H, H$_{trans}$), 1.46 (d, J=13.6 Hz, 1H, H$_{trans}$), 0.84 (d, J$_{P-H}$=8Hz,9H, P(CH$_3$)$_3$), 0.28 (s, 9H, Si(CH$_3$)$_3$), 1 methylenic diastereotopic proton was obscured by the Si(CH$_3$)$_3$ signal, −0.12 (brt, J=12.3 Hz, 1H, CHH(SiMe$_3$)). $^{13}$C NMR (75 MHz, 23° C., C$_6$D$_6$); δ109.4 (d, J$_{C-H}$=155 Hz, central allylic C), 59.6 (dt, J$_{C-P}$=24 Hz, J$_{C-H}$=155 Hz, allylic C trans to P), 54.5 (t, dt, J$_{C-H}$=155 Hz, allylic C cis to P), 16.0 (dq, J$_{P-C}$=25 Hz, J$_{C-H}$=127 Hz, P(CH$_3$)$_3$), 4.2 (q, J$_{C-H}$=117 Hz, Si(CH$_3$)$_3$), −8.8 (dt, JP–C=10 Hz, J$_{C-H}$=115 Hz, CH2SiMe$_3$).

Experiment 8

Preparation of [(C$_3$H$_5$)(PMe$_3$)Ni(Et$_2$O)]$^+$[BAr'$_4$]$^−$

A Schlenk tube was charged with 41.3 mg (0.16 mmol) of (C$_3$H$_5$)(PMe$_3$)Ni(CH$_2$SiMe$_3$) dissolved in 5 ml of diethyl ether. A separate Schlenk tube was charged with H(Et$_2$O)$_2$BAr'$_4$ (159 mg, 0.16 mmol) and cooled to −78° C. The solution containing the nickel complex was transferred via cannula into the cold flask containing the acid. Once all reactants dissolved, 4×10 ml portions of hexane were slowly added to the orange solution under vigorous stirring at −78° C. An orange-yellow solid precipitated immediately. The surnatant was discarded, and the solid was dried under vacuum (143.8 mg, 82%). Upon recrystallization, disproportionation occurred, giving, presumably, (C$_3$H$_5$)Ni(PMe$_3$)$_2$$^+$ and (C$_3$H$_5$)Ni(Et$_2$O)$_2$ $^1$H NMR before recrystallization (250 MHz, 23° C., CD$_2$Cl$_2$); δ7.72 (s, 8H, Ar'), 7.56 (s, 4H, Ar'), 5.67 (m, central allylic H), 4.34 (br, 1H), 3.64 (q, J=7 Hz, 4H, (CH$_3$CH$_2$O)$_2$), 3.25 (br, 1H), 2.65 (br, 1H), 1.85 (br, 1H), 1.50 (t, J=7 Hz, 6H, (CH$_3$CH$_2$O)$_2$), 1.32 (d, J$_{P-H}$=9 Hz, P(CH$_3$)$_3$). Two compounds by $^{13}$C NMR (−78° C.) (H$_2$O and Et$_2$O complexes). $^{13}$C NMR (100 MHz, −78° C., CD$_2$Cl$_2$); δ counterion signals, 115.8 (d, J$_{C-H}$=162 Hz, central allylic C), 114.0 (d, J$_{C-H}$=162 Hz, central allylic C), 73.0 (dt, J$_{C-P}$=18 Hz, J$_{C-H}$=146 Hz, allylic C trans to P), 72.8 (t, J$_{C-H}$=146 Hz, (CH$_3$CH$_2$O)$_2$), 72.2 (dt, J$_{C-P}$17 Hz, J$_{C-H}$=146 Hz, allylic C trans to P), 44.1 (dt, J$_{P-C}$=6 Hz, J$_{C-H}$=157 Hz, allylic C cis to P), 43.7 (dt, JP–C=5 Hz, J$_{C-H}$=157 Hz, allylic C cis to P), 15.2 (q, J$_{C-H}$=126 Hz, (CH$_3$CH$_2$O)$_2$), 13.1 (dq, J$_{P-C=28}$ Hz, J$_{C-H}$=126 Hz, P(CH$_3$)$_3$), 13.0 (dq, JP–C=29 Hz, J$_{C-H}$=126 Hz, P(CH$_3$)$_3$.

Experiment 9

Preparation of (C$_3$H$_5$)NiClP(2-OMe(C$_6$H$_4$))$_3$

A 100-ml flask was charged with [Ni(C$_3$H$_5$)Cl]$_2$ (100 mg, 0.37 mmol) and tris(2-methoxyphenyl)phosphine (262 mg, 0.74 mmol). The two solids were dissolved in Et$_2$O (60 ml), and the resulting solution was stirred overnight. As the reaction proceeded, the product (orange powder) precipitated from the solution. The mixture was filtered; the solid was washed with pentane and dried under vacuum. The yield was 250 mg (69%).

Experiment 10

Preparation of [(C$_3$H$_5$)NiP(2-OMe(C$_6$H$_4$))$_3$ (CH$_3$CN)]$^+$[BAr'$_4$]$^−$ A 50-ml round-bottomed flask was charged with 43 mg (0.088 mmol) of (C$_3$H$_5$)NiCl(2-OMeC$_6$H$_4$) and 78 mg (0.088 mmol) of NaBAr'$_4$. A solution of CH$_3$CN (35 μl, 0.67 mmol) in CH$_2$Cl$_2$ (15 ml) was added. The cloudy solution was stirred at 25° C. for 45 min (NaCl precipitated). Stirring was stopped for 15 minutes, and the solid was filtered off from the orange solution. Solvent and excess acetonitrile were removed at a reduced pressure from the filtrate. The resulting glassy solid was washed twice with 7 ml of pentane and dried under vacuum. The yield of the orange powder obtained was 70 mg (59%).

Experiment 11

Preparation of [(C$_3$H$_5$)Ni(COD)]$^+$[BAr'$_4$]$^-$

A 100-ml round-bottomed flask was charged with 106 mg (0.39 mmol) of [(C$_3$H$_5$)NiCl]$_2$ and 696 mg (0.79 mmol) of NaBAr'$_4$. A solution of 1,5-cyclo-octadiene (2 μl, 16.3 mmol) in Et$_2$O (50 ml) was added. It was stirred at 25° C. for 75 min. The orange-yellow solution was cloudy due to precipitation of NaCl. It was filtered and the solvent and excess COD were removed under vacuum, yielding a yellow powder. It was redissolved in Et$_2$O and filtered. The solvent was removed under vacuum from the filtrate, giving the desired complex as a yellow powder (630 mg, 75% yield). $^1$H NMR (CD$_2$Cl$_2$, 23° C., 300 MHz): d 7.72 (s, 8H, Ar'), 7.56 (s, 4H, Ar'), 5.96 (m, 3H) (2 protons from the COD ligand overlap with the central allylic proton), 5.79 (br m, 2H, COD), 4.50 (dt, J$_{cis}$=7–5 Hz, J=1.25 Hz, 2H$_{Cis}$), 3.06 (d, J$_{trans}$=14–6 Hz, 2H$_{trans}$), 2.75 (m, 4H, COD), 2.48 (m, 4H, COD).

Example 1

A Fischer-Porter tube was charged with 29 mg (0.022 mmol) of (C$_3$H$_5$)NiPCy$_3$(Et$_2$O)+BAr'$_4$. It was placed under 1 atm. (101.3 kPa) of ethylene (the nickel complex reacted in the solid state, turning from a yellow powder to a "wet" appearance due to loss of Et$_2$O). A solution of methyl acrylate (4.5 μl, 50 mmol) in CH$_2$Cl$_2$ (4.5 ml) cooled to −78° C. was added with a syringe. The tube was pressurized to 71 psia (393.0 kPa) of ethylene, and the yellow solution was stirred at 15° C. for 24 hrs. $^1$H NMR (CDCl$_3$) analysis of the reaction mixture reveals the presence of 1-butene (37%), methyl 4-pentenoate (M4P) (49%) and trans-2-dimethylhexene-dioate (DMHD) (14%). The conversion of methyl acrylate to products (M4P and DMHD) was 17% (390 equiv). Thus, the turnover (TO) number for the cross-dimer, M4P, was 250.

GC-mass spectroscopic analysis of the reaction mixture confirms the selective formation of methyl 4-pentenoate (>96%) over methyl 3-pentenoate (M3P, <2%), methyl 2-pentenoate (M2P, not detected) and methyl 2-methyl-butenoate (branched, <2%).

Example 2

A Fischer-Porter tube was charged with 29 mg (0.022 mmol) of (C$_3$H$_5$)NiPCy$_3$(Et$_2$O)+BAr'$_4$. It was placed under 1 atm. (101.3 kPa) of ethylene. A solution of methyl acrylate (4.5 μl, 50 mmol) in CH$_2$Cl$_2$ (4.5 ml) cooled to −78° C. was added with a syringe. The tube was pressurized to 37 psia, (255 kPa) of ethylene, and the yellow solution stirred at 15° C. for 23.5 hrs.

$^1$H NMR (CDCl$_3$) analysis of the reaction mixture reveals the presence of 1-butene (20%), methyl 4-pentenoate (M4P) (57%) and trans-2-dimethylhexene-dioate (DMHD) (23%). The conversion of methyl acrylate to products (M4P and DMHD) was 12% (270 equiv). Thus, the TO number for the cross-dimer, M4P, was 150.

GC-mass spectroscopic analysis of the reaction mixture confirmed the selective formation of methyl 4-pentenoate (>98% yield).

Example 3

A Fischer-Porter tube was charged with 24 mg (0.018 mmol) of (C$_3$H$_5$)NiPCy$_3$(Et$_2$O)+BAr'$_4$, (Ar'=3,5-(CF$_3$)$_2$C$_6$H$_3$). It was placed under 1 atm. of ethylene (101.3 kPa). A solution of methyl acrylate (4.5 μl, 50 mmol) in CH$_2$Cl$_2$ (4.5 ml) cooled to −78° C. was added with a syringe The tube was pressurized to 54 psia {372 kPa) of ethylene, and the yellow solution was heated to 60° C. The pressure increased, but when the desired temperature was reached, the pressure was adjusted to 69 psia (476 kPa). Stirring at this temperature and pressure was continued for 15.5 hrs, at which time the solution was allowed to cool to ambient temperature (ca 1 hour). The solution was extremely viscous indicating the formation of polymer, presumably through a free radical process. The polymer was precipitated in MeOH; GC analysis of the filtrate revealed the presence of cross-dimer M4P along with dimethyl hexenedioates. Comparison of the ratio of the area of the cross-dimer to that of the homo-methyl acrylate dimers with the corresponding ratio obtained in Example 1 indicates a much larger amount of homodimer in the present example (no quantitative data were obtained).

Example 4

A Fischer-Porter tube was charged with 19 mg (0.048 mmol) of (C$_3$H$_5$)Ni(CH$_3$)(PCy$_3$) and 52 mg (0.051 mmol) of H(Et2O)$_2$$^+$BAr'$_4$. It was placed under 1 atm. (101.3 kPa) of ethylene. A solution of methyl acrylate (4.5 ml, 50 mmol, 1040 equiv) in CH$_2$Cl$_2$ (4.5 ml) cooled to −78° C. was added with a syringe. The tube was then pressurized to 69 psia (476 kPa) of ethylene and the yellow solution was stirred at 15° C. for 15 hrs and 40 min. $^1$H NMR (CDCl3) analysis of the reaction mixture reveals the presence of 1-butene (33%), methyl 4-pentenoate (M4P)(6%) and trans-2-dimethylhexenedioate (DMHD) (6%). The conversion of methyl acrylate to products (M4P and DMHD) was 32% (390 equiv). The TO number for the cross-dimer, M4P, was 300. GC-mass spectrometric analysis of the reaction mixture confirms the selective formation of methyl 4-pentenoate (87%) over methyl 3-pentenoate (M3P, 8%), methyl 2-pentenoate (M2P, 4%) and methyl 3-methylbutenoate (branched, 1%).

Example 5

A Fischer-Porter tube was charged with 15 mg (0.038 mmol) of (C$_3$H$_5$)Ni(CH$_3$)(PCy$_3$) and 41 mg (0.040 mmol) of H(Et$_2$O)$_2$$^+$BAr'$_4$$^-$. It was placed under 1 atm. (101.3 kPa) of ethylene. A solution of methyl acrylate (4.5 ml, 50 mmol, 1300 equiv) in Et$_2$O (4.5 ml) was added with a syringe after being cooled to −78° C. The tube was then pressurized to 69 psia (476 kPa) of ethylene, and the yellow solution was stirred at 25° C. for 15 hrs and 40 min. In this example, no quantitative data (TO numbers) were obtained but GC analysis of the reaction mixture indicated a ratio of M4P:M3P:M2P: (branched) of 93:1:4:2.

Example 6

A Schlenk tube was charged with 15 mg (0.038 mmol) of (C$_3$H$_5$)Ni(CH$_3$)(PCy$_3$) and 41 mg (0.040 mmol) of H(Et$_2$O)$_2$$^+$BAr'$_4$. It was placed under 1 atm. (101.3 kPa) of ethylene and cooled to −78° C. at which temperature a solution of methyl acrylate (4.5 ml, 50 mmol, 1310 equiv) in $CH_2Cl_2$ (4.5 ml) was added with a syringe. The tube was placed in a water bath at 25° C., and the yellow solution was stirred for ca 22 hrs. $^1$H NMR ($CDCl_3$) analysis of the reaction mixture reveals the presence of 1-butene, (M4P), and trans-2-dimethyl hexenedioate (DMHD). The conversion of methyl acrylate to products, M4P (57%), and DMHD (43%) was 16% (210 equiv). Thus the TO number for the cross-dimer, M4P, was 80. GC analysis of the reaction mixture confirms the selective formation of M4P (91%) over M3P (1%), M2P (10 6%), and methyl 3-methylbutenoate (branched, 2%).

Example 7

A Fischer-Porter tube was charged with 16 mg (0.040 mmol) of $(C_3H_5)Ni(CH_3)(PCy_3)$ and 43 mg (0.042 mmol) of $H(Et_2O)_2^+BAr'_4^-$. It was placed under 1 atm. (101.3 kPa) of ethylene. A solution of methyl acrylate (4.5 ml, 50 mmol, 1250 equiv.) and tetradecane (1 ml, 3.85 mmol, GC standard) in $CH_2Cl_2$ (4.5 ml) cooled to 0° C. was added with a syringe. The tube was then pressurized to 67 psia (462 kPa) of ethylene, and the yellow solution stirred at 25° C. for 19 hrs. GC analysis of the reaction mixture revealed the presence of 1-butene, cross-dimers and methyl acrylate homo-dimers. The major product was the cross-dimer M4P; it accounted for 91% of the total cross-dimer products (M3P represented 3%, M2P 4% and branched 2%). The TO number for the production of cross-dimers was 395.

Example 8

A Fischer-Porter tube was charged with 35 mg (0.033 mmol) of $(C_3H_5)Ni(COD)+BAr'_4$, and 11 mg (0.039 mmol) of $PCy_3$. It was placed under 1 atm. (101.3 kPa) of ethylene. Then a solution of methyl acrylate (4.5 ml, 50 mmol, 1500 equiv) in $CH_2Cl_2$ (4.5 ml) cooled to –78° C. was added with a syringe. The tube was pressurized to 68 psia (469 kPa) of ethylene and the yellow solution stirred at 25° C. for 15 hrs and 40 min. GC analysis of the reaction mixture revealed the same selectivity for the cross-dimer M4P (>98%).

Example 9

A Fischer-Porter tube was charged with 33 mg (0.031 mmol) of $(C_3H_5)Ni(COD)^+BAr'_4$ and 10 mg (0.036 mmol) of $PCy_3$. Under nitrogen, a solution of methyl acrylate (4.5 ml, 50 mmol, 1610 equiv.) and tetradecane (1 ml, 3.85 mmol, GC standard) in $CH_2Cl_2$ (4.5 ml) was added at room temperature. The tube was then pressurized to 67 psia (462 kPa) of ethylene, and the yellow solution was stirred at 25° C. for 19 hrs. GC analysis of the reaction mixture revealed the presence of 1-butene, cross-dimers and traces of methyl acrylate homo-dimers. The major product was the cross-dimer M4P; it accounts for 97% of the total cross-dimer products (M3P and M2P were not detected while the branched isomer represented ca 3%). The TO number for the production of cross-dimers was 66.

Example 10

A Fischer-Porter tube was charged with 31 mg(0.024 mmol) of $(C_3H_5)NiPCy_3(CH_3CN)^+BAr'_4$. It was placed under 1 atm. (101.3 kPa) of ethylene. A solution of methyl acrylate (4.5 ml, 50 mmol, 2080 equiv.) and tetradecane (2 ml, 7.69 mmol, GC standard) in $CH_2Cl_2$ (4.5 ml) was added with a syringe to this solution cooled to 0° C. The tube was then pressurized to 66 psia (358 kPa) of ethylene, and the yellow solution stirred at 25° C. for 43.5 hrs. GC analysis of the reaction mixture revealed the presence of butenes, cross-dimers, and traces of homo-methyl acrylate diners. The TO number (cross-dimers) was 315, with the following percentage of isomers: 59% (M4P), 34% (branched), 4% (M2P), and 3% (M3P).

Example 11

A Fischer-Porter tube was charged with 34 mg (0.026 mmol) of $(C_3H_5)NiPCy_3(CH_3CN)^+BAr'_4$. It was placed under 1 atm.(101.3 kPa) of ethylene. A solution of methyl acrylate (4.5 ml, 50 mmol, 1890 equiv.) and tetradecane (0.5 ml, 1.92 mmol, GC standard) in $CH_2Cl_2$ (4.5 ml) cooled to 0° C. was added with a syringe. The tube was then pressurized to 68 psia (469 kPa) of ethylene and the yellow solution stirred at 25° C. for 17.25 hrs. GC-mass spectrometric analysis of the reaction mixture reveals the presence of butenes, cross diners, and traces of home-methyl acrylate dimers. The percentage of cross-dimers was as follows: 53% (M4P), 42% (branched), 3% (M2P), and 2% (M3P).

Example 12

A Fischer-Porter tube was charged with 31 mg (0.023 mmol) of $(C_3H_5)NiP(2—OMe(C6H4))_3(CH_3CN)^+BAr'_4$. It was placed under 1 atm. (101.3 kPa) of ethylene. A solution of methyl acrylate (4.5 ml, 50 mmol, 2170 equiv) in $CH_2Cl_2$ (4.5 ml) cooled to –78° C. was added with a syringe. The tube was then pressurized to 67 psia (462 kPa) of ethylene, and the orange solution was stirred at 25° C. for 15 hrs. GC-mass spectroscopic analysis of the reaction mixture indicates the formation of butenes, cross-dimers and homo-methyl acrylate dimers. In this example, no quantitative data (TO numbers) were obtained but GC analysis revealed the presence of cross-dimer products: M4P (34%), M3P (3%), M2P (42%) and branched cross-dimers (21%).

Example 13

Fischer-Porter tube was charged with 36 mg (0.034 mmol) of $(C_3H_5)Ni(COD)^+BAr'_4^-$ and 13 mg (0.037 mmol) of $P(2—OMe(C_6H_4))_3$. It was placed under 1 atm. (101.3 kPa) of ethylene. A solution of methyl acrylate (4.5 ml, 50 mmol, 1470 equiv) in $CH_2Cl_2$ (4.5 ml) cooled to –78° C. was added with a syringe. The tube was pressurized to 66 psia (455 kPa) of ethylene, and the yellow solution was stirred at 25° C. for 22.5 hrs. In this example, no quantitative data (TO numbers) were obtained but GC analysis revealed the presence of 1-butene, and a mixture of cross-dimer products: M4P (36%), M3P (1%), M2P (42%) and branched (21%), and methyl acrylate homo-dimers (ca. 73% trans-2-methyl hexenedioate).

Example 14

Fischer-Porter tube was charged with 26 mg (0.023 mmol) of $(C_3H_5)Ni(PMe_3)(Et_2O)^+BAr'_4^-$ (Ar'=3,5—$(CF_3)_2C_6H_3$). It was placed under 1 atm. (101.3 kPa) of ethylene (the nickel complex reacts in the solid state turning from a yellow powder to a "wet" appearance as a result of loss of $Et_2O$). A solution of methyl acrylate (4.5 ml, 50 mmol, 2170 equiv) in $CH_2Cl_2$ (4.5 ml) cooled to –78° C. was added with a syringe. The tube was then pressurized to 66 psia (455 kPa) of ethylene, and the orange solution was stirred at 25° C. for 17.5 hrs. GC-mass spectroscopic analysis of the reaction mixture indicated the formation of butenes, cross-dimers and homo-methyl acrylate dimers (94% trans-2-methylhexenedioate). In this example, no quantitative data (TO numbers) were obtained but GC analysis revealed a mixture of cross-dimer products: M4P (37%), M3P (57%), M2P (1%) and branched cross-dimers (5%).

The conditions and results of the cross-dimerization Examples 1–14 are summarized below in Tables 1 and 2.

TABLE 1

Reaction of Ethylene with Methyl Acrylate

| Example | Catalyst |
|---|---|
| 1 | $(\eta^3\text{-}C_3H_5)Ni(PCy_3)(OEt_2)^+BAr'_4{}^-$ |
| 2 | as 1 |
| 3 | as 1 |
| 4 | $(\eta^3\text{-}C_3H_5)Ni(PCy_3)(CH_3) + H(OEt_2)^+BAr'_4{}^-$ |
| 5 | as 4 (Et$_2$O solvent) |
| 6 | as 4 (CH$_2$Cl$_2$ solvent) |
| 7 | as 4 (CH$_2$Cl$_2$ solvent) |
| 8 | $(\eta^3\text{-}C_3H_5)Ni(COD)(OEt_2)^+BAr'_4{}^- + PCy_3$ |
| 9 | as 8 |
| 10 | $(\eta^3\text{-}C_3H_5)Ni(PCy_3)(NCCH_3)^+BAr'_4{}^-$ |
| 11 | as 10 |
| 12 | $(\eta^3\text{-}C_3H_5)Ni(P(2\text{-}CH_3OC_6H_4)_3)(NCCH_3)^+BAr'_4{}^-$ |
| 13 | $(\eta^3\text{-}C_3H_5)Ni(COD)^+BAr'_4{}^- + P(2\text{-}CH_3OC_6H_4)_3$ |
| 14 | $(\eta^3\text{-}C_3H_5)Ni(P(CH_3)_3)(OEt_2)^+BAr'_4{}^-$ | cy = cyclohexyl
Ar' = 3,5-(CF$_3$)$_2$C$_6$H$_3$)
COD = 1,5-cyclooctadiene

TABLE 2

Reaction of Ethylene with Methyl Acrylate

| Example | C$_2$H$_4$ Pressure (psia) | (kPa) | Temp °C | Time (hours) | Selectivity (% of cross dimer tha is M4P) | M4P Turnover Number |
|---|---|---|---|---|---|---|
| 1 | 71 | (393) | 15 | 24 | >96 | 250 |
| 2 | 37 | (255) | 15 | 24 | >98 | 150 |
| 3 | 69 | (476) | 60 | 16 | no quantitation | |
| 4 | 69 | (476) | 15 | 16 | 87 | 300 |
| 5 | 69 | (476) | 25 | 16 | 93 | — |
| 6 | 14 | (101) | 25 | 22 | 91 | 80 |
| 7 | 67 | (462) | 25 | 19 | 91 | 395 |
| 8 | 68 | (469) | 25 | 16 | >98 | low |
| 9 | 67 | (462) | 25 | 19 | 97 | 66 |
| 10 | 66 | (455) | 25 | 44 | 59 | 315 |
| 11 | 68 | (469) | 25 | 17 | 53 | — |
| 12 | 67 | (462) | 25 | 15 | 34 | — |
| 13 | 66 | (455) | 25 | 23 | 36 | — |
| 14 | 66 | (455) | 25 | 18 | 37 | — |

What is claimed is:

1. A process for the preparation of methyl 4-pentenoate, said process comprising:

(a) contacting ethylene with methyl acrylate in an oxygen-free and water-free atmosphere in the presence of a nickel II catalyst complex of the structure $[QNiL_1L_2]^+X^-$ wherein Q is $\eta^3$ carbon-based allyl or substituted allyl;

$L_1$ is a monodentate trisubstituted phosphine ligand represented by the formula $PR_1R_2R_3$, wherein each of $R_1$, $R_2$, and $R_3$ is independently a linear, branched, or cyclic monovalent hydrocarbon radical having 1–20 carbon atoms; with the provise that any two of $R_1$, $R_2$, and $R_3$ taken together can form a ring, in which case each is a divalent radical;

$L_2$ is a weakly coordinating ligand;

$X^-$ is a nonreactive anion that either does not coordinate with nickel or weakly coordinates therewith, in the optional presence of a solvent or diluent, wherein any liquid medium that may be present as a solvent or diluent is non-reactive under the conditions of this process and is either not capable of coordinating with nickel or is weakly coordinating therewith; and (b) recovering the crude reaction product produced by said process.

2. The process of claim 1 further including the step of separating methyl 4-pentenoate from the crude reaction product.

3. The process of claim 1 wherein $L_1$ is selected from the group consisting of tricyclohexylphosphine, trimethylphosphine, and triphenyl-phosphine.

4. The process of claim 1 wherein $L_2$ is selected from the group consisting of diethyl ether, tetrahydrofuran, and acetonitrile.

5. The process of claim 1 wherein $X^-$ is selected from the group consisting of $[B(3,5-(CF_3)_2C_6H_3)_4]^-$ and $[B(C_6F_5)_4]^-$.

6. The process of claim 1 which is carried out at a pressure from atmospheric to about 689.5 kPa and at a temperature of about 0° C. to 100° C.

7. The process of claim 6 which is carried out at a pressure of about 96.5 to 379.2 kPa and at a temperature of about 15 to 60° C.

8. The process of claim 1 wherein the nickel catalyst is selected from the group consisting of:

$(\eta^3\text{—}C_3H_5)Ni(PCy_3)(OEt_2)\text{—}BAr'_4{}^-$;

$(\eta_3\text{—}C_3H_5)Ni(PCy_3)(NCCH_3)^+BAr'_4{}^-$;

$(\eta^3\text{—}C_3H_5)Ni(P(2\text{—}CH_3OC_6H_4)_3)(NCCH_3)^+BAr'_4{}^-$; and $(\eta^3\text{—}C_3H_5)Ni(P(CH_3)_3)(OEt_2)^+BAr'_4{}^-$, where Ar is $3,5\text{—}(CF_3)_2C_6H_3\text{—}$, and Cy is cyclohexyl.

9. The process of claim 1 wherein the nickel catalyst is formed in situ and is selected from the group consisting of:

$(\eta^3\text{—}C_3H_5)Ni(PCy_3)(CH_3)+H(OEt_2)_2{}^+BAr'_4{}^-$;

$(\eta^3\text{—}C_3H_5)Ni(COD)+BAr'_4{}^-$; $+PCy_3$; and $(\eta^3\text{—}C_3H_5)Ni(COD)+BAr'_4{}^-+P(2\text{—}CH_3OC_6H_4)_3$;

where Cy=cyclohexyl, Ar'=$3,5\text{—}(CF_3)_2C_6H_3\text{—}$, and COD=1,5-cyclooctadiene.

10. The process of claim 8 wherein the nickel catalyst is $\eta^3\text{—}C_3H_5)Ni(PCy_3)(OEt_2)+BAr'_4{}^-$.

11. The process of claim 1 which is carried out in a solvent.

12. The process of claim 11 wherein the solvent is an aprotic organic solvent.

13. The process of claim 12 wherein the aprotic organic solvent is selected from the group consisting of monochlorobenzene, o-dichlorobenzene methylene chloride, diethyl ether, and tetrahydrofuran.

14. The process of claim 13 which is carried out in the atmosphere of nitrogen.

* * * * *